(12) United States Patent
Takizawa et al.

(10) Patent No.: US 7,692,128 B2
(45) Date of Patent: Apr. 6, 2010

(54) FOCUS CONTROL METHOD FOR AN OPTICAL APPARATUS WHICH INSPECTS A PHOTO-MASK OR THE LIKE

(75) Inventors: Hideo Takizawa, Kanagawa (JP); Koji Miyazaki, Kanagawa (JP)

(73) Assignee: Lasertec Corporation, Kanagawa (JP)

( * ) Notice: Subject to any disclaimer, the term of this patent is extended or adjusted under 35 U.S.C. 154(b) by 125 days.

(21) Appl. No.: 12/002,880

(22) Filed: Dec. 19, 2007

(65) Prior Publication Data

US 2008/0142681 A1 Jun. 19, 2008

(30) Foreign Application Priority Data

Dec. 19, 2006 (JP) ............... 2006-340730

(51) Int. Cl.
*G01J 1/20* (2006.01)
*G01N 21/86* (2006.01)
(52) U.S. Cl. .................. 250/201.1; 250/559.4
(58) Field of Classification Search ... 250/201.2–201.8, 250/208.1; 396/72, 77, 79–82, 89, 111–118, 396/121–123; 348/345, 349–356
See application file for complete search history.

(56) References Cited

U.S. PATENT DOCUMENTS 5,286,963 A * 2/1994 Torigoe ............... 250/201.2

7,193,685 B2 * 3/2007 Miura ............... 355/55

FOREIGN PATENT DOCUMENTS

JP 11-327119 11/1999

* cited by examiner

*Primary Examiner*—Que T Le
*Assistant Examiner*—Pascal M Bui-Pho
(74) *Attorney, Agent, or Firm*—Carrier, Blackman & Associates P.C.; Joseph P. Carrier; William D. Blackman

(57) ABSTRACT

A focus control method able to further correctly control a focal point of an optical system or optical apparatus. A reference system of the system as a whole is set by using a reference pattern for focal point control. A focal point of an optical apparatus for inspecting a sample or measuring a physical quantity of the sample and the focal point of an auto-focus mechanism are matched with the reference system. Then, a displaced object of the auto-focus mechanism is set on a sample surface, a displacement amount of the sample surface from a reference point is measured, and the focal point of an object lens of the optical apparatus is controlled by using the displaced point as an operation point of the control of the auto-focus mechanism. When setting the reference system, the focus is judged by utilizing the Becke effect for the reference pattern.

9 Claims, 7 Drawing Sheets (A)  (B)  (C)

FOCUS CONTROL METHOD FOR AN OPTICAL APPARATUS WHICH INSPECTS A PHOTO-MASK OR THE LIKE

BACKGROUND OF THE INVENTION

1. Field of the Invention

The present invention relates to a focus control method, more particularly relates to a focus control method for controlling the focus of an optical apparatus optically measuring or optically inspecting a physical quantity of a photo-mask, phase shift mask, etc.

2. Description of the Related Art

In the process of production of semiconductor devices or liquid crystal devices, mask patterns formed on a photo-mask are transferred onto a semiconductor wafer by an exposure apparatus. Various types of devices are produced through a development process, an etching process, and various other processes. Along with miniaturization of LSIs, the widths of the patterns of the photo-mask used in the exposure process have been miniaturized as well. Use is being made of phase shift masks as the photo-masks to deal with this miniaturization. Phase shift masks are designed so that a phase difference of π or an odd number times of that is formed between light passing through adjacent pattern elements. The resolution ends up falling from the designed value along with deviation. For this reason, in order to secure the quality of a phase shift mask, the phase shift amount of the phase shift mask is measured by using a phase shift measurement device.

As a device for measuring the phase shift amount of the phase shift mask of a half tone type, a phase shift measurement device using a two-light flux interferometer is known. In this measurement device, light transmitted through a phase shifter interferes with light transmitted through a portion where the half tone film is not formed, and the interference light is received by a photo-detector. Then, the phase shift amount is measured based on an output signal from the photo-detector (see for example Japanese Patent Publication (A) No. 11-327119).

The device for measuring the phase shift amount by using a shearing interferometer can correctly measure the phase shift amount of the phase shifter. On the other hand, along with miniaturization of the LSIs, the diameter of the openings formed in the half tone film has been miniaturized as well. Openings of about 1.0 µm are formed in the half tone film. When the phase shift amount of a phase shift mask having such minute openings formed therein is optically measured, the diffraction phenomenon strongly acts and the phase shift amount to be measured greatly fluctuates even when the focus state of the measurement device slightly displaces from the normal focus position. When the present inventors actually measured the relationship between the focus displacement amount of an optical system and the measured phase shift amount for the phase shift mask having openings with a variety of diameters formed therein, it has found that when the diameters of the openings became 3 µm or less, the measured phase shift amount greatly changed by exactly the very small displacement of the focus of the optical system.

On the other hand, in the phase shift measurement device currently being practically used, the focus of the shearing interferometer is manually adjusted out by an operator while viewing a pattern image displayed on a monitor. For this reason, the actual focus position of the objective lens sometimes displaces from the true focus position, so the measured phase shift amount deviates from the true phase shift amount. This occurs in the same way not only in a case of measuring the phase shift amount of the phase shift mask, but also in a case of optically inspecting for defects and measuring the physical quantities of semiconductor wafers and various types of photo-masks.

SUMMARY OF THE INVENTION

An object of the present invention is to provide a focus control method able to more correctly control the focal state of an optical system or optical apparatus.

The focus control method according to the present invention is A focus control method for controlling a focus state of an optical apparatus for optically inspecting a sample or optically measuring a physical quantity of the sample, said optical apparatus having a stage for supporting the sample, a light source for projecting illumination light toward the sample, an objective lens for receiving the light emitted from the sample, an imaging device for capturing a sample image, an auto-focus mechanism for controlling the position of the objective along its optical axis, and a reference pattern which has Becke effect and is used for focus controlling; comprising the steps of capturing the reference pattern by use of the optical apparatus and adjusting the position of said object lens by using image information output from said imaging device to set the objective in focus state with respect to the reference pattern, setting the reference target point for focus control of the auto-focus mechanism in state that said objective lens is in focus with respect to the reference pattern, wherein, the focal point of the objective lens and the control target point of the auto-focus mechanism are matched with respect to the reference pattern.

In the phase shift measurement device for measuring the phase shift amount of the phase shift mask, in order to measure the phase shift amount with a high precision, high precision focal point control is needed. Therefore, in the present invention, the reference of the focal point control is set by utilizing the Becke effect. Namely, when capturing an image of sample having a refractive index distribution, when the focal point of the imaging device displaces from the sample surface, Becke lines of light and darkness are generated at a portion where the refractive index changes. The Becke lines disappear when the focal point of the imaging device is on the sample surface. By utilizing this Becke effect, the reference point of the focal point control of the imaging device can be set with a high precision. Therefore, in the present invention, an absolute reference system of the focus control of the system as a whole is set by using the reference pattern for the control of the focal point in which the Becke effect is judged, and the focal point of the optical apparatus and the control target point of the auto-focus mechanism are matched with respect to the related absolute reference system. Then, the displaced object of the auto-focus mechanism is set on the sample, and the object lens of the optical apparatus is controlled in drive by the focal point control signal output from the auto-focus mechanism during the inspection or measurement. By constituting the apparatus in this way, the reference of the focal point control of the optical apparatus for inspecting or measuring the sample and the reference of the focal point control of the auto-focus mechanism are set to the same conditions, therefore the object lens of the optical apparatus will be constantly be controlled in drive to an operation point set by the absolute reference system during the inspection or measurement of the sample.

In a preferred embodiment of the focus control method according to the present invention, the reference pattern has a plurality of grooves or concave portions formed in a transparent substrate, and judging whether or not the objective lens is in focus with respect to the reference pattern on the base of the captured image of the reference pattern. The reference pattern for the focus control can be mounted on a stage supporting the sample or can be directly formed on the sample surface by etching in a case where the sample is a sample having a transparent substrate like a photo-mask.

In the present invention, the absolute reference for defining the reference of the focal point control of the system as a whole is set, and the focal point of the optical apparatus for inspecting or measuring a sample and the focal point of the auto-focus mechanism are matched with the set absolute reference. Therefore, it is possible to focus the focal point of the optical apparatus with respect to the sample with a high precision during the inspection or measurement of the sample. In particular, the reference of the focal point of the system as a whole is set by utilizing the Becke effect, therefore further high precise focus control becomes possible.

BRIEF DESCRIPTION OF THE DRAWINGS

These and other objects and features of the present invention will become clearer from the following description of the preferred embodiments given with reference to the attached drawings, wherein.

DESCRIPTION OF THE PREFERRED EMBODIMENTS

Figure 1:
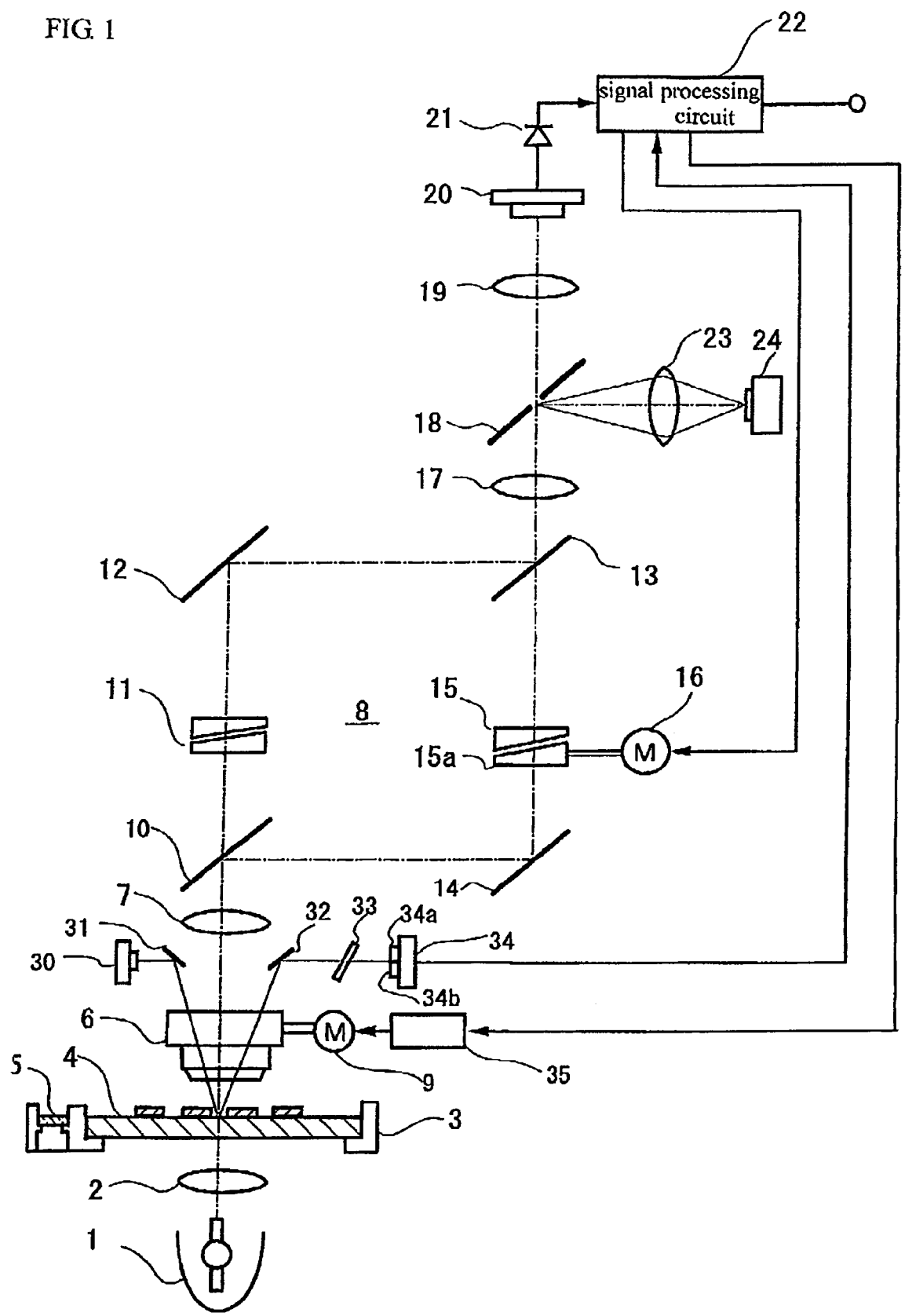
FIG. 1 is a diagram showing an example of a phase shift measurement device for which a focus control method according to the present invention is performed.

In the present example, an explanation will be given of the focus control of a device for measuring the phase shift amount of a phase shift mask. FIG. 1 is a diagram showing an example of a phase shift measurement device for which the focus control method according to the present invention is executed. Illumination light emitted from an illumination light source 1 is projected toward a phase shift mask 4 arranged on an XY stage 3 via a focus lens 2. As the illumination light source 1, use is made of a light source emitting light having the same wavelength as the wavelength of the projection beam which is actually used in an exposure apparatus. For example, when the exposure apparatus uses an ArF laser, the light obtained by splitting light generated from a heavy hydrogen lamp by a prism and having a wavelength of 193.4 nm is used as the illumination light. The XY stage 3 carries a reference pattern 5 for the focus control. The related reference pattern is set as the reference position of the focus control.

The light emitted from the phase shift mask 4 is received by an objective lens 6, passes through a relay lens 7, and strikes a shearing interferometer 8. The objective lens 6 is mounted so that it can displace along its optical axis direction by a servo motor 9.

The shearing interferometer 8 forms laterally offset images of the mask pattern, combines the two formed laterally offset images with each other, and outputs a combined laterally offset interference image. As the shearing interferometer, use can be made of a Mach-Zehnder interference optical system, Nomarski prism, and other various types of shearing interference optical systems. In the present example, use is made of the Mach-Zehnder interferometer. The image light striking the Mach-Zehnder interferometer 8 is split by a half mirror 10, then the image beam passes through a first double wedge prism 11 and total internal reflection mirror 12 and strikes a half mirror 13. The other image beam passes through a total internal reflection mirror 14 and second double wedge prism 15 and strikes the half mirror 13. The first double wedge prism 11 and second double wedge 15 are adequately set, predetermined shearing amounts are given, and two laterally offset images are formed. One wedge prism 15a of the second double wedge prism 15 is connected to a linear motor 16, moves in a direction perpendicular to the optica axis, and gives 1 cycle's worth of phase modulation with respect to the passing image light.

Two image beams laterally offset by exactly the predetermined shearing amounts are combined by the half mirror 13, then pass through a relay lens 17 and a total internal reflection mirror 18 having an opening at its center portion and strike an imaging lens 19. The combined laterally offset interference image is imaged onto a two-dimensional imaging device 20 by the imaging lens 19. The two-dimensional imaging device 20 has a plurality of light receiving elements aligned in a two-dimensional array. The image light striking each light receiving element is transformed to an electric signal. The electric signals formed by the light receiving elements are sequentially read out, pass through an amplifier 21, and are supplied to a signal processing circuit 22.

In the present example, the image light reflected at the total internal reflection mirror 18 is focused onto a two-dimensional CCD 24 via another imaging lens 23 enabling to view an inspection portion of the phase shift mask 4. Note that the total internal reflection mirror 18 having an opening at the center is hot a component indispensable for the present invention, but is provided according to a need.

Figure 2:
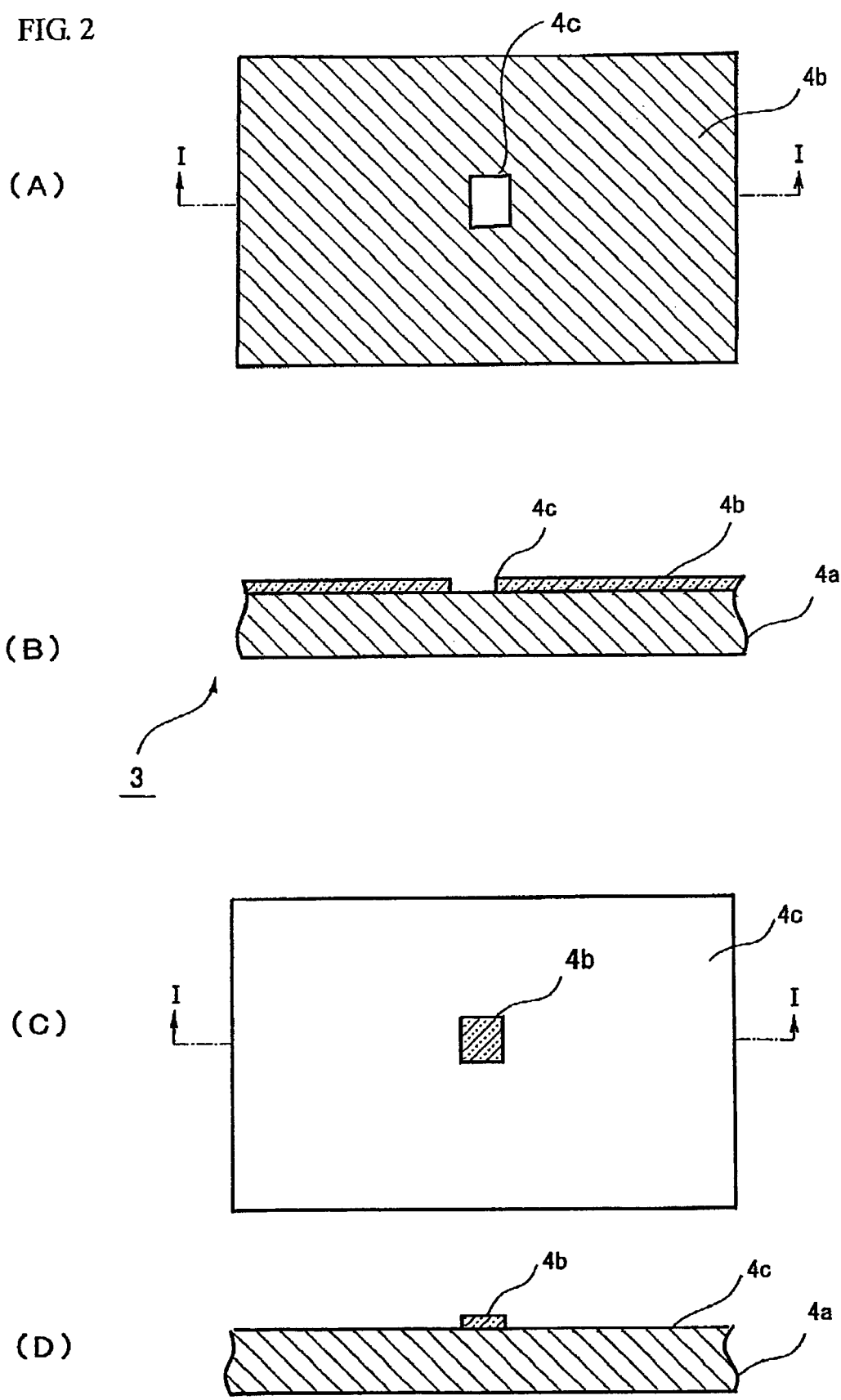
FIGS. 2A to 2D are line drawings showing an example of a mask pattern of a phase shift mask.

FIGS. 2A to 2D show an example of a mask pattern of a phase shift mask to be inspected. In the present example, the phase shift amount of a half tone type phase shift mask is measured. FIG. 2A is a plan view, while FIG. 2B is a sectional view taken along a line I-I. The half tone type phase shift mask 4 has a quartz substrate 4a, a half tone film 4b constituting the phase shifter formed on that, and a rectangular opening 4c formed in a portion of the half tone film 4b. In the present specification, the portion where the half tone film is formed is used as a phase shifter portion, the portion where the half tone film is not formed, but the quartz base plate is exposed (for example, the opening 4c) is used as a non-phase shift portion, and the phase difference between the light transmitted through the phase shifter portion and the light transmitted through the non-phase shift portion, that is, the phase shift amount, is measured. Note that, as shown in FIGS. 2C and 2D, a mask pattern in which the phase shifter portion is formed in the wide non-phase shift portion where the half tone film is not formed is measured in the same way. Note that the mask pattern shown in FIG. 2 is used for convenience of explanation. It is possible to measure phase shift amounts of various types of actual masks.

Figure 3:
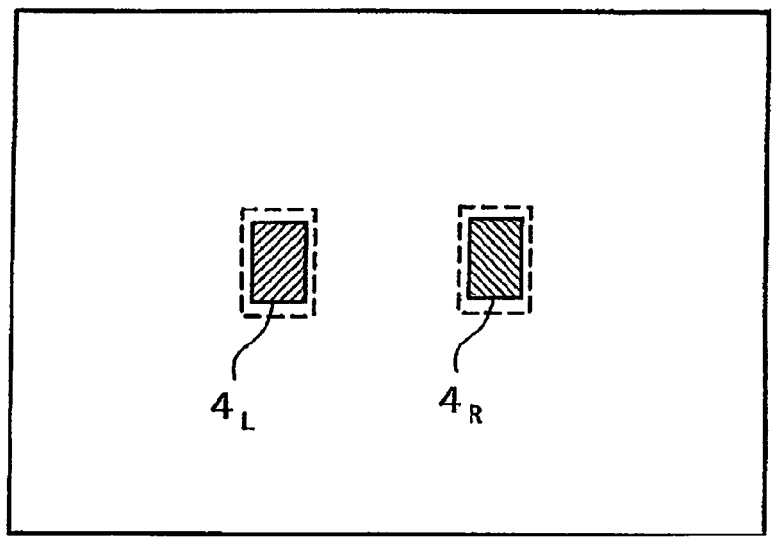
FIG. 3 is a diagram showing two laterally offset pattern images.

For clarifying the explanation, in the present example, an explanation will be given of the method of measurement of the phase shift amount by using the mask pattern shown in FIGS. 2A and 2B as an example. FIG. 3 is a diagram diagrammatically showing two laterally offset interference images of the opening 4c focused onto the two-dimensional imaging device 17. By suitably setting the shearing amount by the set angle adjustment of the double wedge prism 11 of the shearing interferometer, two laterally offset images of the opening 4c of the mask pattern are prevented from being superimposed on each other. Here, the image of the opening formed on left side in the figure is defined as 4L, while the image of the opening portion formed on the right side is defined as 4R.

Figure 4:
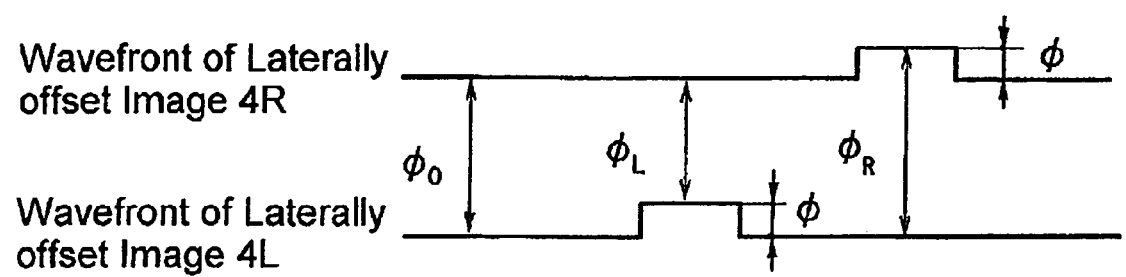
FIG. 4 is a graph showing the relationship of wavefronts of pattern images.

FIG. 4 is a diagram diagrammatically showing the relationship of wavefronts of the two laterally offset images of the opening 4c formed by the shearing interferometer. In FIG. 4, φo indicates a phase difference of interfering two wavefronts, φL indicates the phase difference of the laterally offset image 4L, φR indicates the phase difference of the laterally offset image 4R, and φ indicates the found phase shift amount of the phase shifter (halftone film). According to the relationship between the wavefronts of the two laterally offset images, the following equations stand among the phase amounts φ, φR, φL, and φo:

$$\phi o = \phi L + \phi$$

$$\phi R = \phi o + \phi$$

The phase shift amount φ of the phase shifter is given according to the following equation:

$$\phi = (\phi R - \phi L)/2$$

Accordingly, the phase shift amount of the phase shifter is found from the phase amounts φL and φR of the two laterally offset images of the mask pattern (opening 4c) included in the laterally offset interference image.

Next, a processing routine in the signal processing circuit 22 will be explained.

Step 1

The phase shift mask to be inspected is arranged on the XY stage, and a mask pattern suited to the measurement of the phase shift amount is selected. Next, the laterally offset interference image of the selected mask pattern is captured and displayed on the monitor. At this time, preferably the XY stage is adjusted to position the two laterally offset images of the mask pattern at the center of the monitor.

Step 2

The operator defines pixel regions forming measurement areas for the laterally offset images of the mask pattern displayed on the monitor. When defining the measurement areas, as indicated by the broken lines of FIG. 3, preferably regions having sizes larger than the laterally offset pattern images are defined. At this time, the measurement regions are defined for two laterally offset pattern images 4R and 4L. As pixels of the measurement areas (light receiving elements), for example pixel regions of 20×20 are defined.

Step 3

Figure 5:
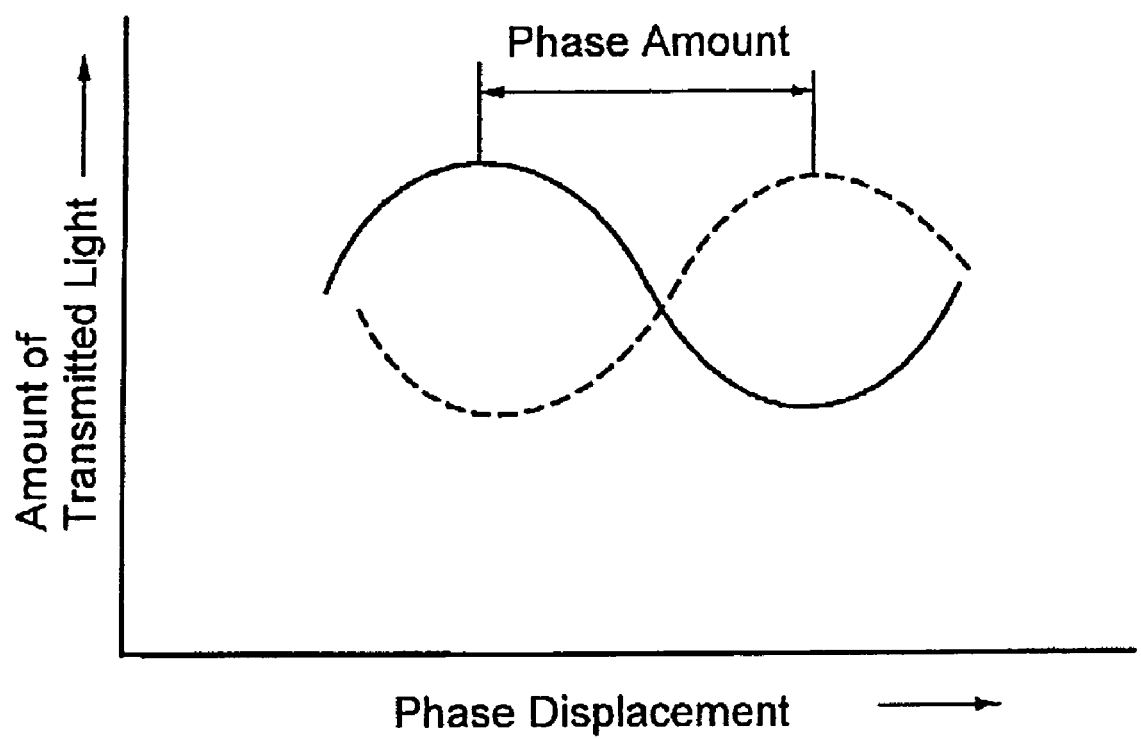
FIG. 5 is a graph showing an example of phase modulation data.

One wedge prism of the second double wedge prism is moved 1 cycle's worth for phase modulation. The obtained phase modulation data is stored in a memory as first phase modulation data $P1(i,j)$ for each pixel for two laterally offset images 4L and 4R. Simultaneously, amplitude data is calculated as well and stored in the memory as first amplitude data $I1(i,j)$. Note that the obtained first phase modulation data $P1(i,j)$ is indicated by a solid line in FIG. 5.

Step 4

Next, the XY stage is moved, an area of a uniform pattern where only the halftone film is formed (the openings are not formed) or an area in which the halftone film is not formed is selected, the wedge is moved 1 cycle's worth, second phase modulation data is acquired for each pixel and stored in the memory and second amplitude data is calculated. Note that in a case where a portion of uniform pattern is obtained even when the XY stage is not moved, pixels composing the relevant region are defined as the measurement area. The obtained second phase modulation data is defined as $P2(i,j)$, and the calculated amplitude value is defined as $I2(i,j)$. The second phase modulation data is indicated by a broken line in FIG. 5.

Step 5

Next, based on the equations shown below, the phase amount P(i,j) and amplitude value I(i,j) of the mask pattern are found for each pixel (light receiving element):

$$P(i,j)=P1(i,j)-P2(i,j)$$

$$I(i,j)=I1(i,j)-I2(i,j)$$

Step 6

Next, the data of any pixel (light receiving element) having a peculiar value of the phase amount P(i,j) and amplitude value I(i,j) found for each pixel for the two laterally offset pattern images is excluded from the measurement target. Namely, when the diffraction light from a pattern edge portion etc., multi-reflection light, or the like is incident, the phase amount or amplitude value of the related pixel greatly changes from the values of the peripheral pixels. Accordingly, any pixel where one or both of the phase amount and amplitude value greatly changes from values of peripheral pixels is excluded from the measurement target.

As the method of excluding a pixel having a peculiar value, various methods are used. For example the phase amount of the light receiving element exceeding a predetermined threshold value using the value of the pixel (light receiving element) at the center of the measurement region as a reference is excluded, and a mean value of phase amounts of remaining light receiving elements is found and defined as the phase amount. Alternatively, differentiation may be carried out, the differentiated values may be compared with a threshold value, and a mean value of phase amounts having differentiated values within a predetermined threshold value may be found. Further, the same processing may be carried out for the amplitude value, the phase amount of any light receiving element having a peculiar amplitude value may be excluded, and the average of the phase amounts of remaining light receiving elements may be found as well. The phase amounts of the two pattern images obtained in this way are output as $P_R$ and $P_L$.

Step 7

Finally, a phase shift amount P of the phase shift mask is calculated based on the following equation, then the processing ends.

$$P=(P_R-P_R)/2$$

Next, the focus control will be explained. First, the auto-focus mechanism will be explained. Referring to FIG. 1, the auto-focus mechanism has a light source 30 generating a measurement beam. The light source 30 can be constituted as for example a laser beam source. The measurement beam generated from the laser beam source is reflected at a total internal reflection mirror 3, passes through the objective lens 6, and strikes the phase shift mask 4 of the displaced object. The measurement beam is reflected at the surface of the phase shift mask 4, reflected at a second total internal reflection mirror 32, passes through a positioner 33, and strikes a split type photodiode 34 having two light receiving elements 34a and 34b. Output signals from the split type photodiode 34 are supplied to the signal processing device 22, where a focus control signal for controlling the drive of the objective lens at the signal processing device 22 is produced. Note that, as a technique of producing the focus control signal, for example, the Foucault method, knife-edge method, and various other techniques are known. It is also possible to use various other focus controlling means. It is also possible to use, in place of the split type photodiode, a linear image sensor having a plurality of light receiving elements arranged in a line to produce a focus error signal by using the signal output from the light receiving elements.

In FIG. 1, when the surface of the phase shift mask 4 displaces along the optical axis direction of the objective lens, the reflected light from the phase shift mask displaces in the up/down direction in the figure. Along with this displacement, the light amounts of reflected light incident upon the light receiving elements 34a and 34b of the split type photodiode 34 change. These two light amount values are detected at the signal processing device 22 and normalized so that they are not influenced by reflectance of the target so as to produce the focus control signal for controlling the focus state of the objective lens 6. The focus control signal is supplied to a drive circuit 35 to drive the motor 9. In this way, focus control is carried out so that the object lens 6 is always focused with respect to the displaced object during the inspection or measurement.

Next, the focus control at the time of the start of measurement or inspection will be explained. Before the focus control, the XY stage 3 is moved and the reference pattern 5 for focus control is positioned in a field of the objective lens 6, the illumination light is projected from a rear side of the reference pattern 5, and the image of the reference pattern is captured by the phase shift measurement device.

Figure 6:
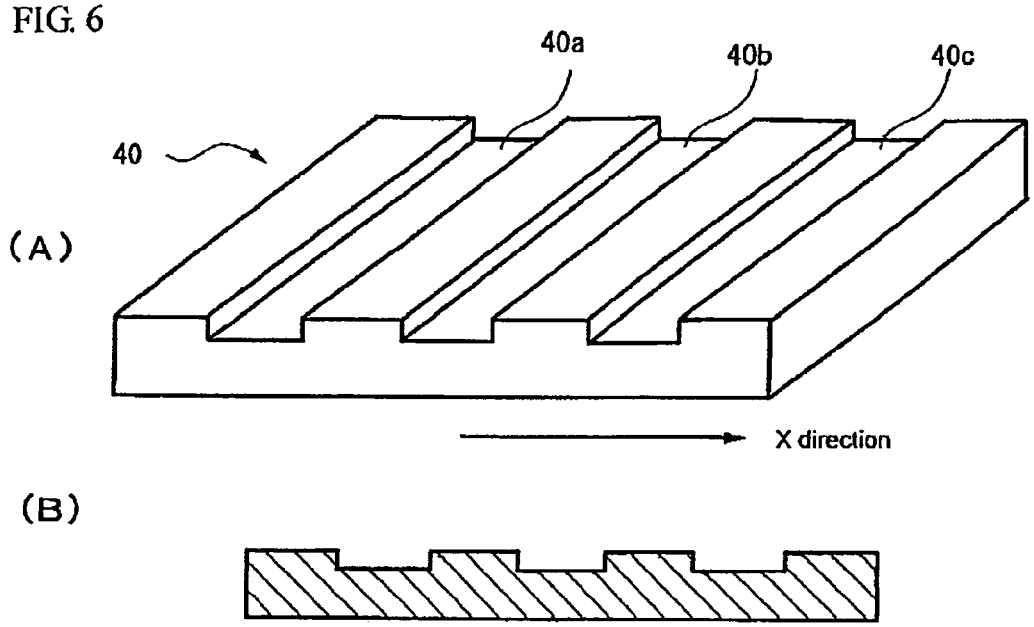
FIGS. 6A and 6B are diagrams showing a reference pattern for controlling a focal point.

FIGS. 6A and 6B are diagrams showing an example of the reference pattern, in which FIG. 6A is a perspective view and FIG. 6B is a sectional view. The reference pattern has three grooves 40a to 40c formed in one surface of a transparent base plate 40 by etching. Widths of these grooves are about 1 to 2 μm. The depth of the grooves are set so that a phase difference of about 30 to 180° is formed between the light transmitted through the groove portions and the light transmitted through the non-groove portions. For example, when the wavelength of the measurement light (the illumination light generated from the light source 1) is 193 nm, the depth is set to about 40 to 200 nm.

Figure 7:
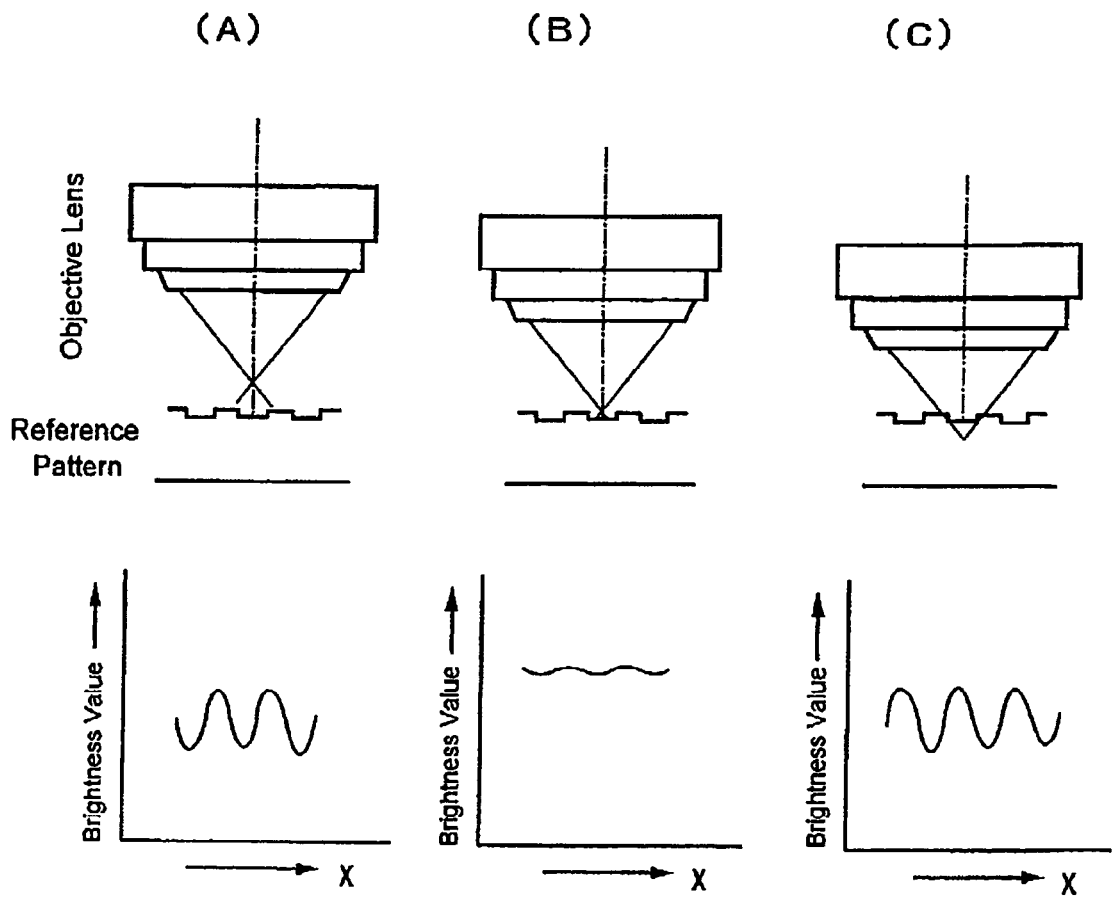
FIGS. 7A to 7C are diagrams showing relationships between focal point states of an optical apparatus and luminance distributions of captured images.

FIGS. 7A to 7C show the focus state of the objective lens 6 and brightness distribution in an X-direction of the image of the reference pattern captured by the imaging device 20. FIG. 7A shows a state where the focal point of the imaging device is above the phase shift mask, FIG. 7B shows a state where the focal point of the imaging device is on the surface of the phase shift mask, and FIG. 7C shows a state where the focal point is below the surface of the phase shift mask. The graphs at the bottom side of FIG. 7 show brightness distributions in the X-direction of images captured by the imaging device. When the focal point of the imaging device displaces upward or downward from the surface of the phase shift mask, a pattern of light stripes and dark strips, that is, Becke lines, are captured in accordance with the refractive index distribution of the reference pattern. On the other hand, when the focal point of the imaging device is on the surface of the reference pattern, the stripe pattern of light and darkness vanishes due to the Becke effect and an almost flat brightness distribution is detected. Accordingly, if the objective lens 6 is displaced upward or downward by only a minute distance (for example, a distance of about tens of nm) from a certain reference position along the optical axis direction, the brightness distribution of the reference pattern image is detected, and the position where the brightness distribution becomes almost flat is detected as the focus position of the objective lens. By utilizing such Becke effect, it is possible to position the focal point of the imaging device on the surface of the phase shift mask with a high resolution of about tens of nm.

After adjusting the position of the objective lens so that the objective lens is in focus onto the reference pattern, the measurement beam is emitted from the light source 30 of the auto-focus mechanism and made to strike the reference pattern via the objective lens. The reflection light from the reference pattern is received by the split type photodiode, and the positioner 33 is adjusted so that the light amounts received by the receiving elements 34a and 34b become equal to each other. In this state, the objective lens is focused with respect to the reference pattern and, at the same time, the reference target point of the auto-focus mechanism is set on the reference pattern. Thereby, the reference target point of the auto-focus mechanism coincides with the focal point of the objective lens.

Next, the XY stage 3 is moved, and the position to be measured of the phase shift mask is located in the view field of the objective lens. At this time, the surface of the phase shift mask displaces along the optical axis direction with respect to the reference pattern, therefore the displacement output is output from the split photodiode 33 of the auto-focus mechanism to the signal processing device. The signal processing device produces the focus control signal corresponding to the displacement amount from the set reference point, and the focus control signal is supplied to the drive circuit 35 to drive the motor 9, and then the objective lens becomes in focus on the surface of the phase shift mask. By setting in this way, the objective lens 6 is controlled by using the reference pattern acting as the absolute reference, and the focal point of the optical apparatus is constantly focused onto the sample surface during the inspection or the measurement of the sample.

The setting of the operation point of the auto-focus mechanism is prosecuted when the photo-mask to be measured is exchanged or when a long time passes after the last setting. By setting the focus in this way, the focal point of the imaging device is constantly controlled with respect to the absolute reference of the focus control during the inspection or measurement for a short period or a long period, and it becomes possible to perform correct inspection or measurement even when the pattern of photo-mask etc. is miniaturized.

FIGS. 8A and 8B are diagrams showing a modification of the reference pattern, in which FIG. 8A is a perspective view and FIG. 8B is a plan view. The reference pattern has a transparent substrate 50 and three light shield patterns 51a to 51c constituted by chromium layers are formed on the transparent substrate 50. Each of four regions 52 to 55 defined by the three light shield patterns is divided into two, and concave portions 52a to 55a are alternately formed. The depth of these concave portions is set so that a phase difference of about 90° is formed with respect to the light transmitted through the concave portions 52a to 55a and the light transmitted through the non-concave portions. For example, when the wavelength of the measured beam is 193 nm, the depth of the concave portions, that is, the etching amount, is set to about 90 to 100 nm.

Figure 8:
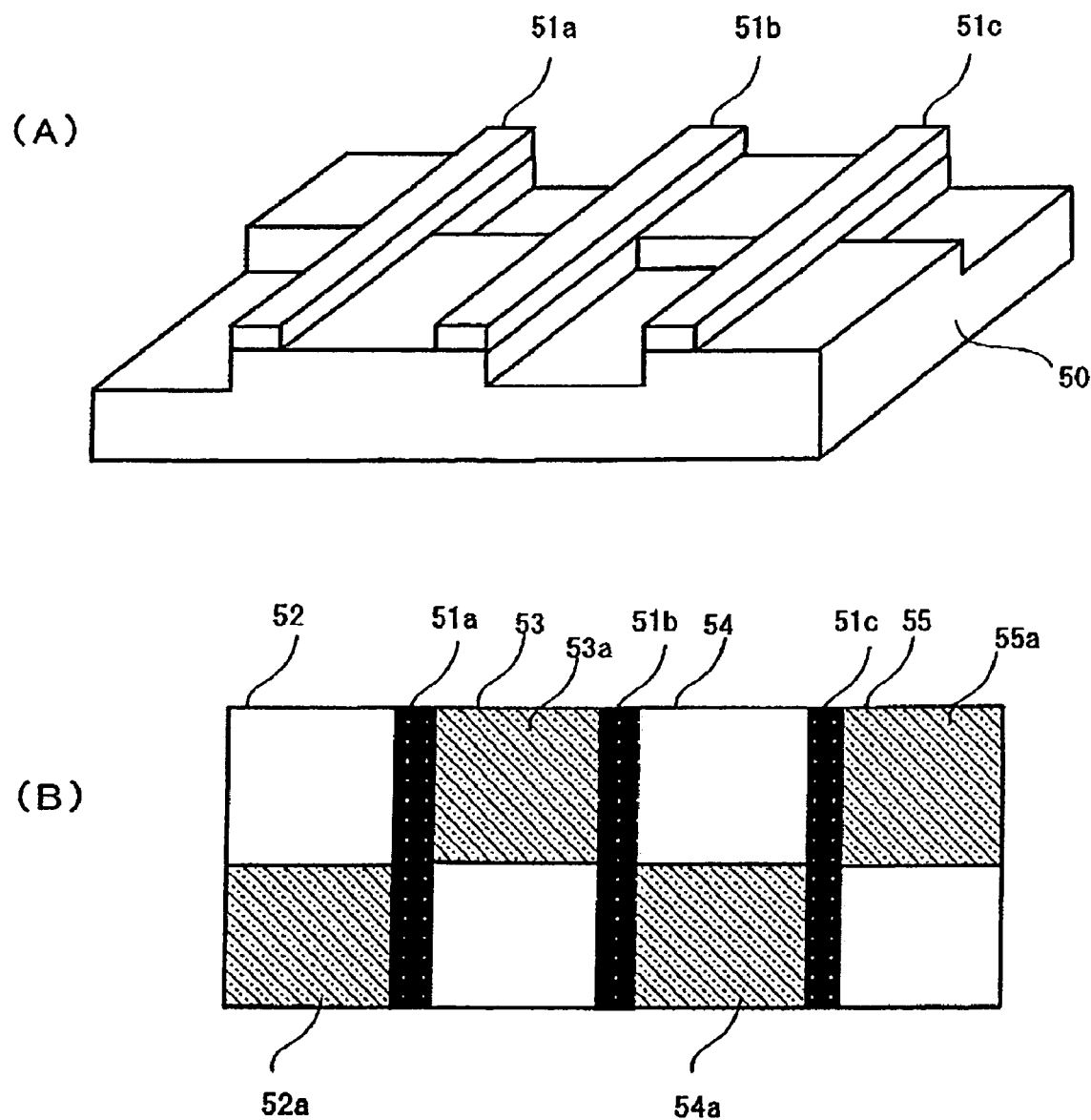
FIGS. 8A and 8B are diagrams showing a modification of the reference pattern for controlling the focal point.
Figure 9:
FIGS. 9A to 9C show captured images obtained by an imaging device of the optical apparatus capturing the reference patterns shown in FIGS. 8A and 8B.
Figure 9:
Figure 9:
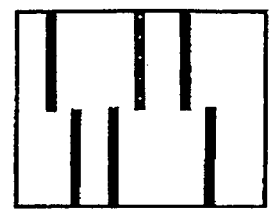

FIGS. 9A to 9C show captured images of the reference pattern obtained by capturing the reference patterns shown in FIG. 8 with use of the imaging device of the optical apparatus.

FIGS. 9A to 9C show captured images of reference patterns in a state where the focal point of the imaging device is in the front focus state (the focal point is located on the imaging device side from the surface of the reference pattern), is in focus state, and is in the rear focus state (the focal point is located on the rear side from the surface of the reference pattern). When the focal point of the imaging device, that is, the focal point of the objective lens, is on the reference pattern, the light shield pattern of the chromium is captured in a straight line state. In the front focus state and the rear focus state, the light shield pattern displaces at a boundary between the etching portion and the non-etching portion. Accordingly, the focal point of the imaging device can be focused based on the form of the captured image of the reference pattern captured by the imaging device.

The present invention is not limited to the embodiment mentioned above. Various modifications and alterations are possible. For example, in the embodiment mentioned above, the reference pattern for controlling the focal point was provided on the stage supporting the sample, but it is also possible to directly form this on the photo-mask or other transparent substrate by etching.

Further, it is possible to utilize various forms of mechanisms as the auto-focus mechanism. For example, in the embodiment mentioned above, the measurement beam was made to strike the sample via the object lens, but it is also possible to employ a constitution making the measurement beam directly strike the sample surface and directly receive the reflected light from the sample surface by a photo-detector.

In the embodiment mentioned above, the explanation was given by using a device for measuring the phase shift amount of the phase shift mask as an example, but it is possible to also apply the present invention to focus control of a device for optically measuring or optically inspecting physical quantities of the photo-mask, liquid crystal photo-mask, semiconductor wafer, etc.

Further, in the embodiment mentioned above, the explanation was given by using the example of measuring the phase shift amount as the physical quantity, but it is also possible to measure the transmittance of the light shield pattern formed on the photo-mask by using the phase shift measurement device mentioned above. Further, it is possible to apply the focus control method according to the present invention to a measurement device for optically measuring not only the phase shift amount and transmittance, but also other physical quantities of the sample as well.

The invention claimed is:

1. A method for setting a reference point of focus control of an optical apparatus which comprises a two-dimensional imaging device having a plurality of light receiving elements aligned in two-dimensional array for capturing a transmittance image of a sample and optically inspecting the sample or optically measuring a physical quantity of the sample using the transmittance sample image captured by said two-dimensional imaging device, a stage for supporting the sample, an illumination light source for projecting illumination light toward the sample from a rear side of the sample, an objective lens for receiving transmittance light transmitted through the sample, a two-dimensional imaging device for receiving light emitted from the objective lens to form a two-dimensional image of the sample, an auto-focus mechanism for controlling the position of the objective lens along its optical axis during inspection or measurement of the sample, and a reference pattern which has Becke effect;

the method comprising the steps of:
positioning the reference pattern within the field of the objective lens,
projecting the illumination light emitted from the illumination light source toward the reference pattern from a rear side of the reference pattern,
capturing an image of the reference pattern by use of the two-dimensional imaging device to form a two-dimensional image of the reference pattern,
sequentially moving the objective lens along its optical axis to detect the position of the objective lens along its optical axis when Becke line disappears from the image of the reference pattern captured by the two-dimensional imaging device, and
setting a control target point of the auto-focus mechanism with respect to a position of the objective lens at which the Becke line disappears from the image of the reference pattern.

2. A method as set forth in claim 1, wherein the reference pattern has a plurality of grooves or concave portions formed in a transparent substrate.

3. A method as set forth in claim 1, wherein the reference pattern is mounted on the stage for supporting the sample or directly formed on the sample surface.

4. A method as set forth in claim 1, wherein said auto-focus mechanism comprises an illumination light source for projecting illumination beam toward the sample via the objective lens, a light detector for receiving reflected light from the sample, a device producing a focus control signal based on the output signal from the light detector, and a driver for driving the objective lens along its optical axis using the focus control signal.

5. A method as set forth in claim 4, wherein said light detector comprises a split type photodiode having two light receiving elements.

6. A method as set forth in claim 1, wherein said sample is a phase shift mask, a shearing interferometer is arranged between the objective lens and the imaging device, said two-dimensional imaging device captures laterally offset interference images of the sample, and the optical apparatus measures a phase shift amount of a phase shift mask based on the laterally offset interference images.

7. A method as set forth in claim 6, wherein said light source for projecting illumination light is arranged in one side of the stage and the two-dimensional imaging device is arranged in other side of the stage, wherein the two-dimensional imaging device captures the transmittance image of the phase shift mask.

8. A method as set forth in claim 1, wherein said sample is a phase shift mask or a photo-mask.

9. A method as set forth in claims 8, wherein said sample is a photo-mask, and wherein a transmittance of a light shielding pattern of the photo-mask is measured as the physical quantity of the sample.

* * * * *

UNITED STATES PATENT AND TRADEMARK OFFICE
CERTIFICATE OF CORRECTION

PATENT NO.        : 7,692,128 B2
APPLICATION NO.   : 12/002880
DATED             : April 6, 2010
INVENTOR(S)       : Takizawa et al.

It is certified that error appears in the above-identified patent and that said Letters Patent is hereby corrected as shown below:

Title page:
    After "*Primary Examiner—*" change "Que T" to --Que T.--.
    After "*Assistant Examiner—*" change "Pascal M" to --Pascal M.--.

Column 1:
    Line 9, change "more particularly" to --and more particularly--.
    Line 31, change "half tone type" to --halftone-type--.
    Line 35, change "half tone film" to --halftone film--.
    Line 36, change "photo-detector" to --photodetector--.
    Line 44, change "half tone film"to --halftone film--.
    Line 45, change "half tone film" to --halftone film--.

Column 2:
    Line 11, change "is A focus" to --is a focus--.
    Line 18, change "position of the objective" to --position of the objective lens--.
    Line 22, change "said object lens" to --said objective lens--.
    Line 24, change "objective in focus state" to --objective lens in focus--.
    Line 26, change "mechanism in state that" to --mechanism so that--.
    Line 37, change "of sample having" to --of a sample having--.
    Line 52, change "the object lens" to --the objective lens--.
    Line 59, change "the object lens" to --the objective lens--.
    Line 60, change "will be constantly be controlled" to --will be constantly controlled--.

Column 3:
    Line 15, change "Becke effect, there-" to --Becke effect; there- --.

Column 4:
    Line 24, change "optica axis" to --optical axis--.
    Line 46, change "center is hot" to --center is not--.
    Line 50, change "half tone type" to --halftone-type--.
    Line 52, change "half tone type" to --halftone-type--.

Signed and Sealed this

Fourteenth Day of September, 2010

David J. Kappos
*Director of the United States Patent and Trademark Office*

Line 53, change "half tone film" to --halftone film--.
Line 55, change "half tone film" to --halftone film--.
Line 56, change "half tone film" to --halftone film--.
Lines 57-58, change "half tone film" to --halftone film--.
Lines 65-66, change "half tone film" to --halftone film--.

Column 5:
Line 14, change "on left side" to --on the left side--.

Column 6:
Line 65, change "mirror 3" to --mirror 31--.

Column 7:
Lines 2-3, change "split type" to --split-type--.
Line 4, change "split type" to --split-type--.
Line 12, change "split type" to --split-type--.
Line 21, change "split type" to --split-type--.
Line 43, change "The depth of the grooves are set" to --The depth of the grooves is set--.
Line 62, change "and dark strips" to --and dark stripes--.

Column 8:
Line 16, change "split type" to --split-type--.

Column 9:
Line 29, change "photo-detec-" to --photodetec- --.

Column 10:
Line 17, change "when Becke line" to --when the Becke line--.
Line 32, change "jecting illumination beam" to --jecting an illumination beam--.
Line 39, change "split type" to --split-type--.
Line 49, change "arranged in one side" to --arranged on one side--.
Line 51, change "arranged in other side" to --arranged on another side--.
Line 56, change "in claims 8" to --in claim 8--.